United States Patent
Frasier et al.

(10) Patent No.: US 7,625,339 B2
(45) Date of Patent: Dec. 1, 2009

(54) RETRACTOR BLADE EXTENDER TOWER

(75) Inventors: William J. Frasier, New Bedford, MA (US); Connie P. Marchek, Foxboro, MA (US); Timothy Beardsley, Kingston, MA (US); Michael Zajack, Marshfield, MA (US)

(73) Assignee: Depuy Spine, Inc., Raynham, MA (US)

( * ) Notice: Subject to any disclaimer, the term of this patent is extended or adjusted under 35 U.S.C. 154(b) by 640 days.

(21) Appl. No.: 11/014,615

(22) Filed: Dec. 15, 2004

(65) Prior Publication Data

US 2006/0129033 A1     Jun. 15, 2006

(51) Int. Cl.
*A61B 1/32* (2006.01)
(52) U.S. Cl. .................................. 600/215
(58) Field of Classification Search .............. 600/215, 600/213–214, 210, 234, 228, 201, 227, 229, 600/191; 128/20; 248/352, 125.8, 405, 188.4; 33/712, 809, 511, 512, 513, 514.1, 514.2, 33/515, 823, 824, 825; 606/191
See application file for complete search history.

(56) References Cited

U.S. PATENT DOCUMENTS

| 186,191 | A | * | 1/1877 | Archer .................. 248/405 |
| 721,800 | A | * | 3/1903 | Heatly .................. 33/512 |
| 1,416,896 | A | * | 5/1922 | Simmons ............... 248/352 |
| 1,949,280 | A | * | 2/1934 | Lester .................. 33/823 |
| 2,670,732 | A | * | 3/1954 | Nelson ................. 600/234 |
| 2,841,876 | A | * | 7/1958 | Pittenger .............. 33/838 |
| 3,024,510 | A | * | 3/1962 | Malesko ............... 411/555 |
| 3,807,049 | A | * | 4/1974 | Zajac .................. 33/823 |
| 4,116,232 | A | * | 9/1978 | Rabban ................ 600/215 |
| 4,380,999 | A | * | 4/1983 | Healy .................. 600/228 |
| 4,899,452 | A | * | 2/1990 | Schafer ................ 33/296 |
| 5,000,163 | A | * | 3/1991 | Ray et al. ............. 600/233 |
| 5,060,393 | A | * | 10/1991 | Silverman et al. ....... 33/512 |
| 5,121,753 | A | * | 6/1992 | Paez ................... 600/587 |
| 5,195,506 | A | * | 3/1993 | Hulfish ................ 600/204 |
| 5,379,758 | A | * | 1/1995 | Snyder ................. 600/213 |

(Continued)

OTHER PUBLICATIONS

DePuy Spine, a Johnson & Johnson Company. "Surgical Technique: Pipeline Expandable Access System CONCORDE—MIS T.L.I.F. Technique Guide Featuring the Pipeline Expandable Retractor and Concorde Instrumentation." pp. 1-30, date of publication unknown.

(Continued)

*Primary Examiner*—Ralph A Lewis
(74) *Attorney, Agent, or Firm*—Lahive & Cockfield, LLP; Kevin J. Canning

(57) ABSTRACT

A blade extending tower for setting blade depth on retractors having telescoping or extending blades. The blade extending tower features a base, a column extending from the base, and mating features on the column configured to engage the blades of a retractor to extend the blades to a desired blade depth. Blade depth of the retractor is set buy sliding the retractor onto the blade extending tower such that the mating features of the blade extending tower engage the blades or the retractor, stopping the blades progression while the rest of the retractor continues along the length of the column. Thus the blades of the retractor are extended from the retractor to a depth determined by the configuration of the blade extending tower.

4 Claims, 11 Drawing Sheets

U.S. PATENT DOCUMENTS

| | | | |
|---|---|---|---|
| 5,573,495 A * | 11/1996 | Adler | 600/204 |
| 5,688,223 A * | 11/1997 | Rosendahl | 600/215 |
| 5,746,743 A * | 5/1998 | Greenberg | 606/96 |
| 5,769,782 A * | 6/1998 | Phan | 600/202 |
| 5,928,139 A | 7/1999 | Koros et al. | |
| 5,967,974 A * | 10/1999 | Nicholas et al. | 600/233 |
| 6,113,535 A * | 9/2000 | Fox et al. | 600/228 |
| 6,139,493 A | 10/2000 | Koros et al. | |
| 6,558,318 B1 * | 5/2003 | Daniel et al. | 600/213 |
| 2003/0176867 A1 * | 9/2003 | Long et al. | 606/79 |
| 2006/0020284 A1 * | 1/2006 | Foley et al. | 606/191 |

OTHER PUBLICATIONS

Nuvasive, Creative Spine Technology. "Maxcess TLIF Surgical Tecnique" 23 pages, date of publication unknown.

* cited by examiner

RETRACTOR BLADE EXTENDER TOWER

FIELD OF THE INVENTION

The present invention relates to retractors used in spinal surgery. More particularly, the present invention relates to a blade extending tower for setting blade depth on retractors.

BACKGROUND OF THE INVENTION

In surgical procedures trauma to the patient and damage to the tissue needs to be minimized as much as possible. To achieve this result surgeons try to keep incisions as small as possible when performing surgical procedures. However, it is necessary that the surgeon performing the delicate surgery have a clear view of the operating field. A variety of retractors are available to keep an incision open and provide a clear field of view of the operation. The retractor is inserted in the incision to hold organs, muscles, arteries and other tissue out of the way and provide a clear view of the spinal region being operated on. The retractor displaces only a small volume when inserted in the incision before it is opened, or "spread" to provide a clear view of the operating field.

However, a common problem with retractors is that no single length of blade is suitable for all patients. Therefore several different size blades must be provided to accommodate different patients. This requires a multitude of different blades being provided and sterilized for an operation. Also, when the retractor is placed in the patient, the surgeon may have to experiment with different length retractor blades until he gets the right length. This increases the length of the operation and the danger of increased trauma to the patient.

Telescoping blades may be adjusted or set in situ when the retractor has already been inserted. Blindly extending the blades after the retractor has been inserted can cause additional trauma as the blades may cut or otherwise damage organs, tissues, or muscles as they are pushed aside as the blades are extended, and may not retract the muscles completely. Thus, what is needed is a means of setting the depth of the blades before the retractor is inserted.

SUMMARY OF THE INVENTION

The present invention provides a retractor blade extender tower for extending retractor blades to the proper depth before inserting the retractor in the body of the patient. By placing a retractor on the retractor blade extender tower the user is able to extend the blades of the retractor to a predetermined depth in a quick and efficient manner.

In accordance with a first aspect, a blade extending tower comprises a base, a column extending from the base; and mating features on the column configured to engage the blades of a retractor to extend the blades to a desired blade depth.

In accordance with another aspect, there is a method of setting blade depth on a retractor having at least one extending blade. The method comprises determining an amount of extension for the at least one extending blade, and positioning the retractor on an instrument to extend the at least one extending blade of the retractor an amount approximate to the determined amount of extension for the at least one extending blade.

In accordance with another aspect, a blade extending tower comprises a base, a column extending substantially perpendicular from the base, mating features on the column configured to engage the blades of a retractor to extend the blades to a desired blade depth, and an adjustable stop configured to be positioned along the length of the column to stop the progress of a retractor placed onto the blade extending tower.

In accordance with another aspect, there is a method of setting blade depth on a retractor having extending blades. The method comprises providing a blade extending tower comprising a base, a column extending substantially perpendicular form the base, mating features on the column configured to engage the blades of a retractor to extend the blades to a desired blade depth, and an adjustable stop configured to be positioned along the length of the column to stop the progress of a retractor placed onto the blade extending tower; adjusting the stop to provide a desired depth for the retractor blades; and sliding the retractor onto the blade extending tower to the adjusted stop to extend the blades of the retractor.

DETAILED DESCRIPTION OF THE INVENTION

The present invention will be described below relative to an illustrative embodiment. Those skilled in the art will appreciate that the present invention may be implemented in a number of different applications and embodiments and is not specifically limited in its application to the particular embodiments depicted herein.

The present invention provides a retractor blade extender tower for extending retractor blades to the proper depth before inserting the retractor in the body of the patient. By placing a retractor on the retractor blade extender tower the user is able to extend the blades of the retractor to a predetermined depth in a quick and efficient manner.

Figure 1:
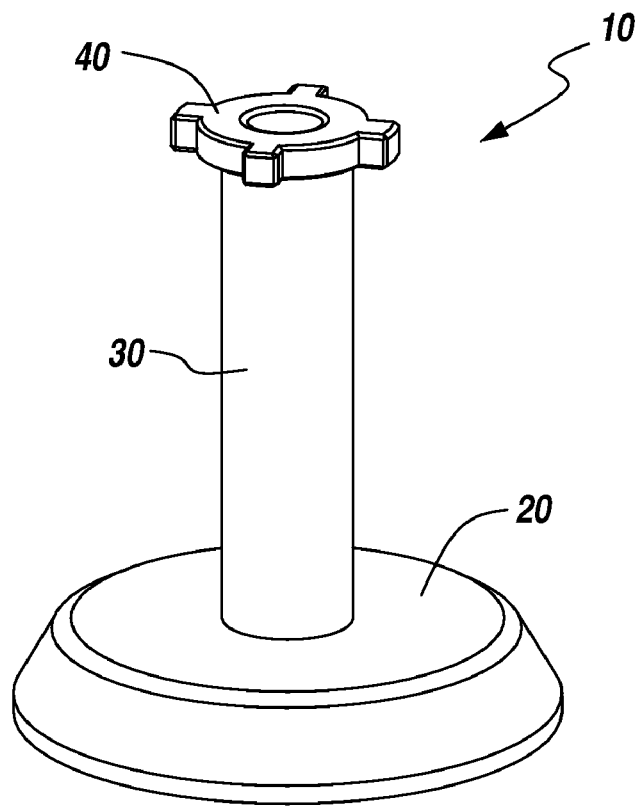
FIG. 1 is a perspective view of a blade extending tower according to an embodiment of the invention.

In one embodiment illustrated by FIG. 1, a blade extending tower 10 of the present invention has a base 20, a column 30 extending substantially perpendicular from the base 20, and mating features 40 on the column 30 configured to engage the blades of a retractor. The blade extending tower 10 is preferably formed of stainless steel or other surgical grade materials. In some embodiments the blade extending tower 10 is formed as a solid piece. In other embodiments the base 20, column 30, and mating features 40 may be separated from each other for cleaning and storage. For example, the column 30 may screw or pressure fit into the base 20. Likewise the mating features 40 may screw or pressure fit onto the column 30. The blade extending tower 10 may be made in different sizes to be used with different sized retractors. An example of a different sized blade extending tower 10A can be seen in FIG. 2 wherein the column 30A is shorter than the column 30 of the blade extending tower 10 of FIG. 1.

Figure 2:
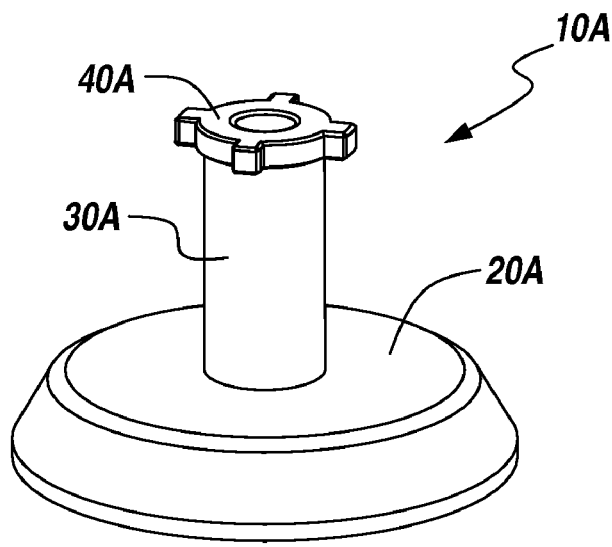
FIG. 2 is a perspective view of a blade extending tower according to another embodiment of the invention.
Figure 3:
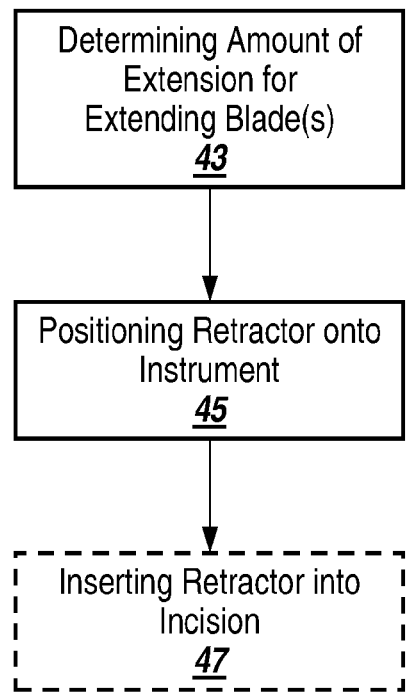
FIG. 3 is a block diagram flow chart depicting one embodiment of a method of setting blade depth on a retractor having telescoping or extendable blades.

The base 20 is typically round and substantially wider in diameter than the column to provide a stable foundation for the blade extending tower. Preferably the base 20 is of substantial weight so as to increase stability when placed on a surface. In certain embodiments the base 20 has surface configurations to make it fit more comfortably and increase grip in a user's hand. In some embodiments the base 20 of the blade extending tower 10 may be detached from the column 30 for cleaning and easier storage. In this manner the base 20 may also be interchanged with other bases to configure the blade extending tower 10 for a particular application. Other sizes, shapes and configurations will be apparent to one skilled in the art given the benefit of this disclosure The column 30 is typically of a size and shape to mate with a retractor having telescoping or extending blades. Exemplary retractors having telescoping blades are disclosed in U.S. Provisional Patent Application Ser. No. 60/530,565, filed Dec. 18, 2003, and U.S. patent application Ser. No. 10/815,182, filed Mar. 31, 2004. The column 30 is typically substantially cylindrical in shape but may also be rectangular or any other shape suitable to engage a retractor to set blade depth. In certain embodiments the height of the column 30 determines the blade depth of a retractor. Preferably the height of the column is between 30 and 125 mm, more preferably between 30 and 95 mm. In certain embodiments the height of the column 30 is adjustable. In some embodiments, the column 30 has graduation marks along its length allowing a user to determine blade depth visually. In certain embodiments the column 30 may detached from the base 20 for storage and cleaning. In this manner the column 30 may also be interchanged with other columns to configure the blade extending tower 10 for a particular application. Other sizes, shapes and configurations will be apparent to one skilled in the art given the benefit of this disclosure The mating features 40, as shown in FIGS. 1 and 2, are located at the end of the column 30 opposite the base 20. The mating features 40 in the illustrated embodiment are teeth that are configured to engage or mate with the blades of the retractor. In the present embodiment, there are four teeth but there may be any number of teeth. Typically, there are a number of teeth sufficient to engage the number of blades to be extended. The mating features may also serve as a guide or key for aligning the placement of the retractor upon the blade extending tower 10. The mating features 40 may also be tabs, flanges, knobs, protrusions or any other configuration suitable for engaging or mating with the blades of the retractor. In certain embodiments the mating features 40 may detached from the column 30 for storage and cleaning. In this manner the mating features 40 may also be interchanged to configure the blade extending tower 10 for a particular application. Other sizes, shapes and configurations will be apparent to one skilled in the art given the benefit of this disclosure FIG. 3 is a flow chart depicting one embodiment of a method of setting blade depth on a retractor having at least one extending blade. First, the amount of extension for the extending blade is determined, step 43. Then the retractor is positioned or placed on an instrument, such as the blade extending tower of the present invention, to extend the at least one extending blade of the retractor an amount approximate to the determined amount of extension for the at least one extending blade, step 45. In some embodiments, this step may also involve selecting an instrument of an appropriate height to extend the extending blades based on the determined amount of extension for the at least one extending blade. In embodiments, wherein the instrument, such as the blade extending tower, has an adjustable stop; the stop may be adjusted to a distance from a base of the instrument approximate to the determined amount of extension for the at least one extending blade. Multiple blades on a retractor may also be extended in this manner. In certain embodiments the method further involves inserting the retractor into an incision made in a patient, step 47.

Figure 3A:
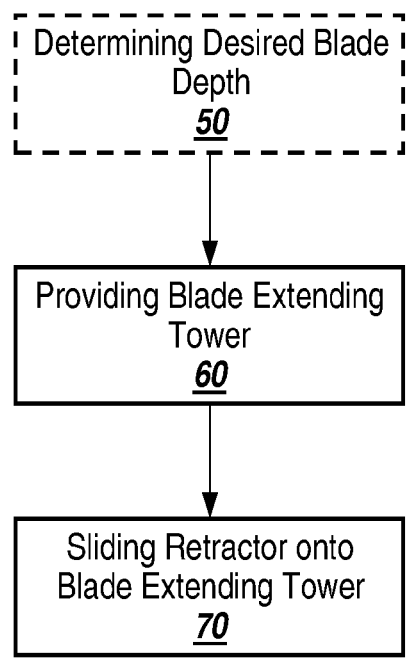
FIG. 3A is a block diagram flow chart depicting another embodiment of a method of setting blade depth on a retractor having telescoping or extendable blades using the blade extending tower of FIGS. 1 and 2.

FIG. 3A is a flow chart depicting another embodiment of a method of setting blade depth on a retractor having telescoping or extendable blades. The first step 60 is providing a blade extending tower 10 consisting of a base 20, a column 30 extending substantially perpendicular from the base 20, and mating features 40 on the column 30 configured to engage the blades of a retractor. In certain embodiments, there may be several blade extending towers 10 of varying heights and configuration from which the user, here a surgeon, selects the most appropriate for the particular application. The next step 70 is sliding the retractor onto the blade extending tower to extend the telescoping or extendable blades. In certain embodiments the method further includes the step 50 of determining a desired blade depth. This is typically accomplished by the surgeon who will measure the required blade depth from the patient's skin level to the surgical site targeted.

Figure 4:
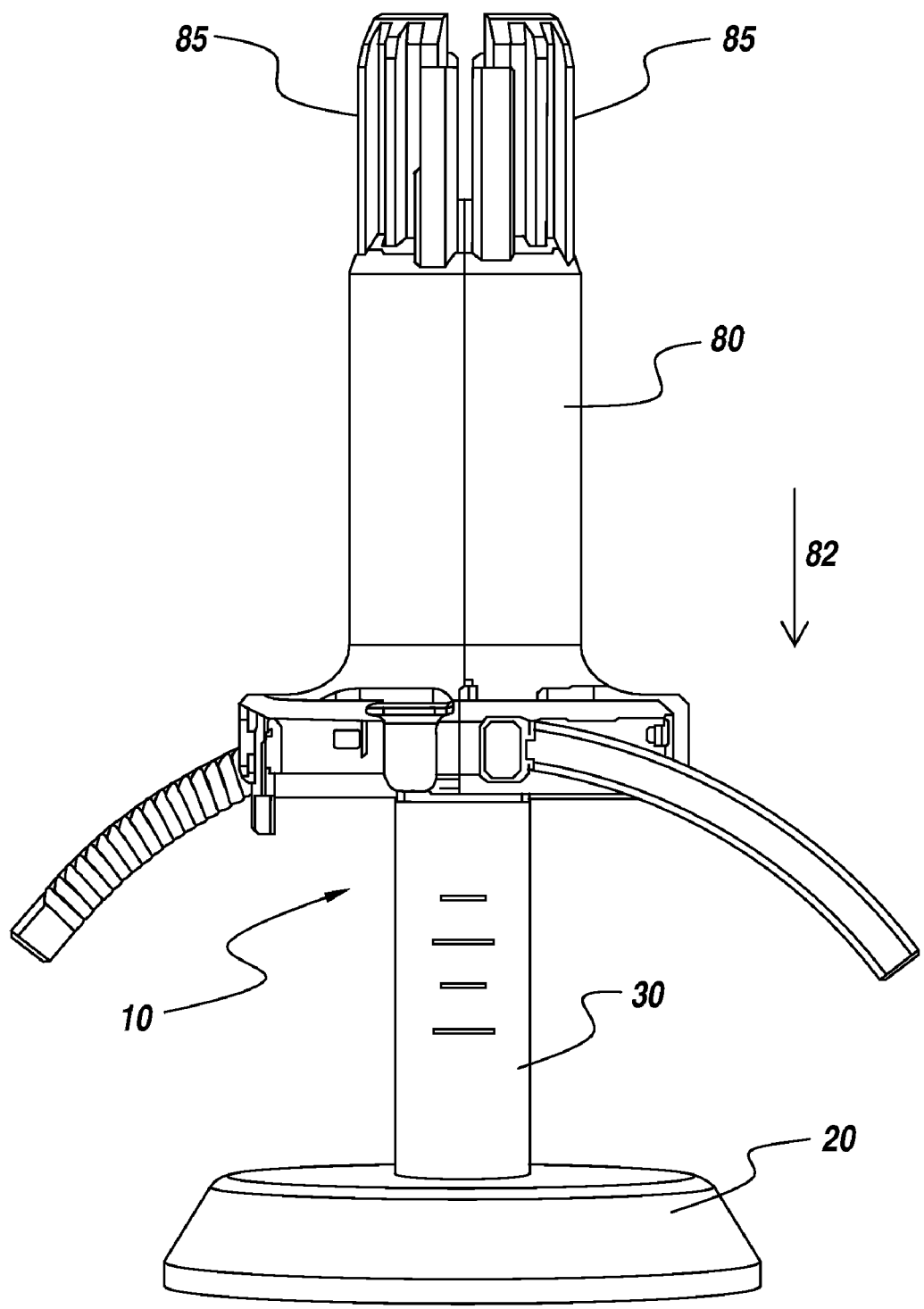
FIG. 4 is a visual depiction of a retractor being placed or slid onto a blade extending tower of the present invention to set blade depth.

FIG. 4 is a visual depiction of a retractor 80 being placed or slid onto the blade extending tower 10 as set forth in step 70 in FIG. 3. In operation when the retractor 80 is pushed or slid onto the column 30 of the blade extending tower 10 in the direction indicated by arrow 82, the mating features 40 engage the blades 85 of the retractor 80 effectively stopping the movement of the blades 85 while the rest of the retractor 80 continues along the length of the column 30 in the direction of arrow 82 until stopped by the base 20. In this manner the blades 85 are extended to the depth determined by the height of the column 30.

Figure 5:
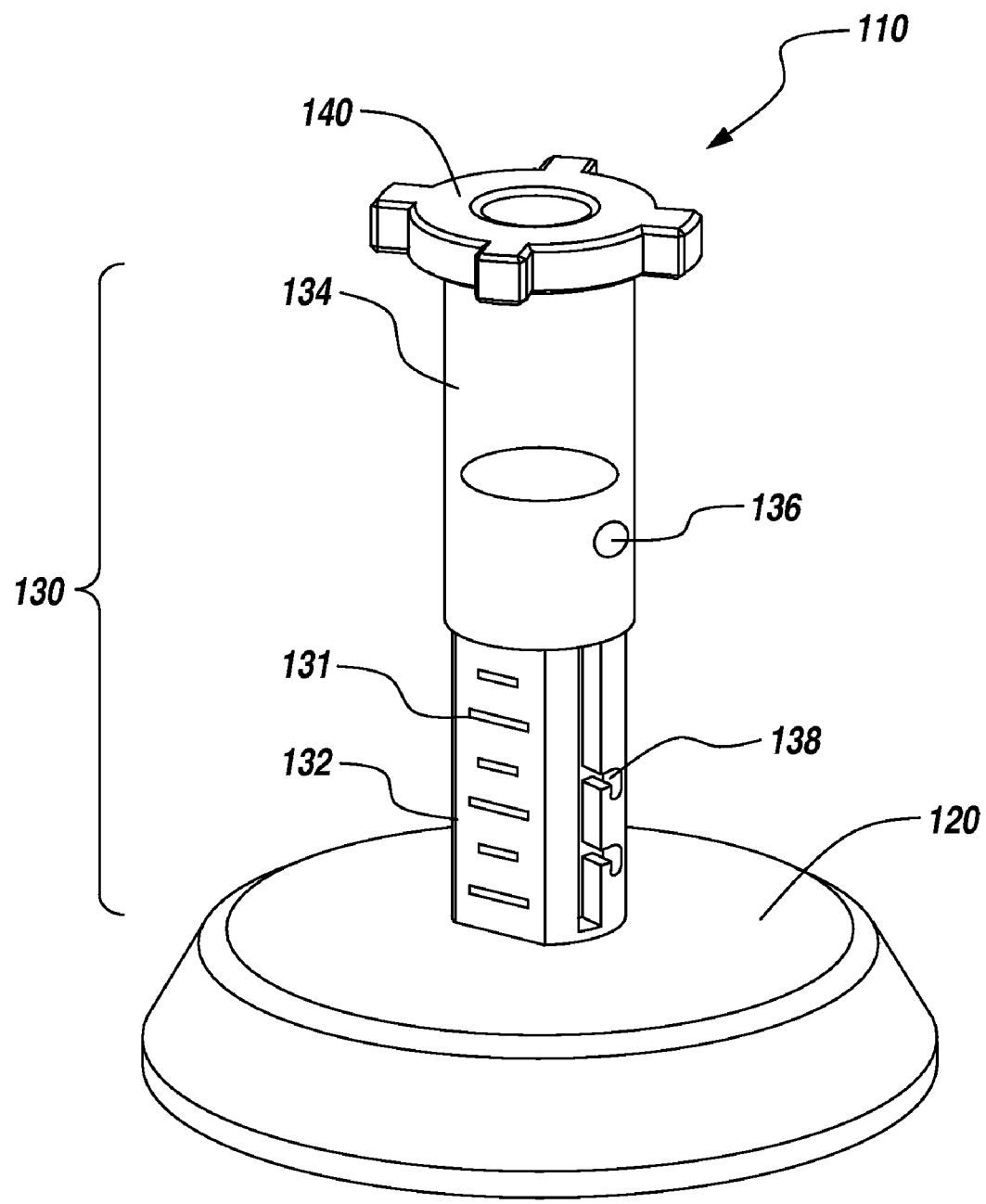
FIG. 5 is a perspective view of a blade extending tower having an adjustable column according to another embodiment of the invention.

In another embodiment as depicted in FIG. 5, the blade extending tower 110 features a base 120, and adjustable column 130 extending substantially perpendicular from the base 120, and mating features 140 on the adjustable column 130. In this embodiment, the adjustable column 130 has a lower portion 132 attached to the base 120 and an upper portion 134 configured to slide over the lower portion 132. The top portion 134 of the column 130 has a pin 136 that rides in a groove in the lower portion 132 of the column 130. The upper portion 134 of the column 130 will be rotated about the lower portion 132 allowing the pin 136 to slide into a slot, here a j-shaped slot 138, thereby permitting the setting of the depth of the retractor blades 85. This embodiment further comprises depth graduations 131 on the column 130 to assist in setting the depth.

The adjustable column 130 may have other configurations that allow the height of the column to be adjusted. For example, the lower portion 132 and upper portion 134 may have mating thread that allow the upper portion 134 to be screwed onto the lower portion 132 to set the height of the column 130 for the desired blade depth. Other configurations and implementations for adjusting the column will be apparent to one skilled in the art given the benefit of this disclosure.

Figure 6:
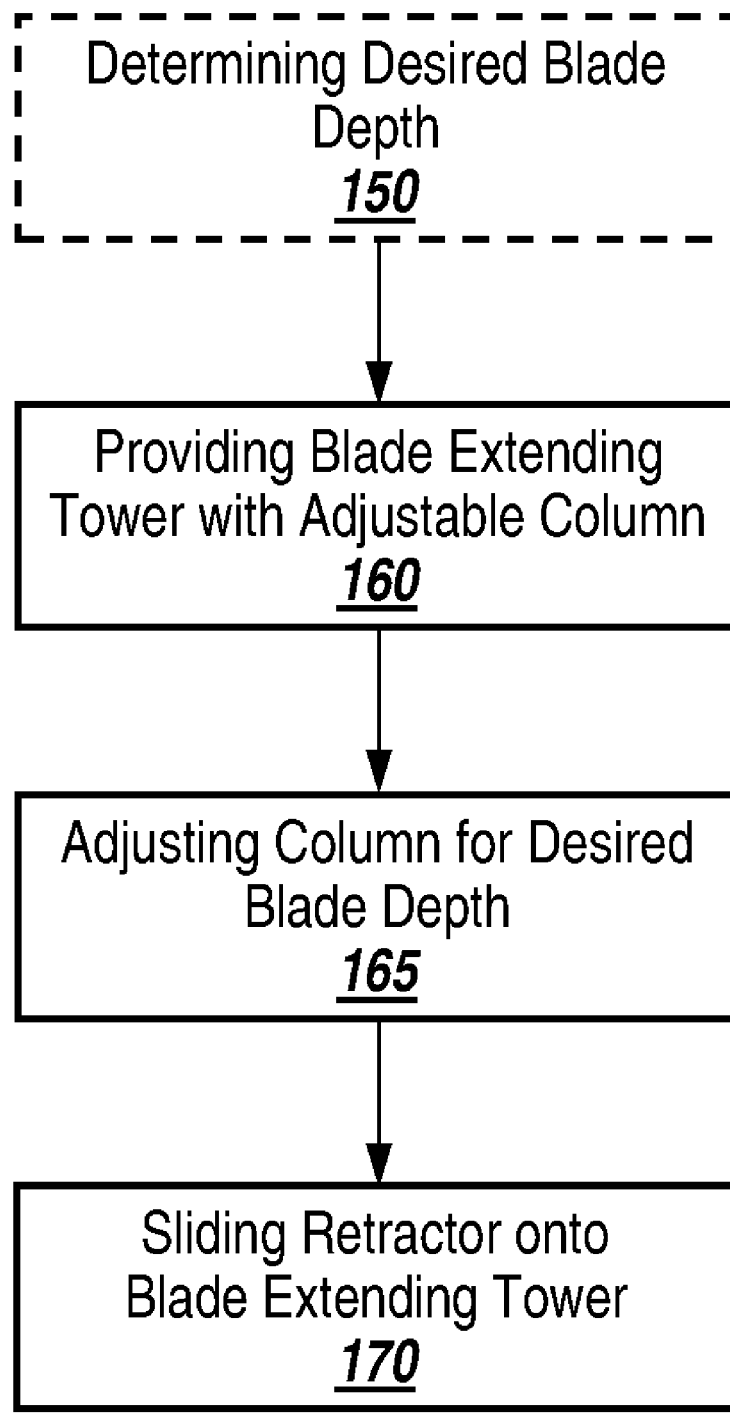
FIG. 6 is a flow chart depicting one embodiment of a method of setting blade depth on a retractor having telescoping or extendable blades using the blade extending tower of FIG. 5.

FIG. 6 is a flow chart depicting one embodiment of a method of setting blade depth on a retractor having telescoping or extendable blades using the blade extending tower of FIG. 5. The first step 160 is providing a blade extending tower consisting of a base 120, an adjustable column 130 extending substantially perpendicular from the base 120, and mating features 140 on the column 130 configured to engage the blades of a retractor. The next step 165 is adjusting the height of the column 130 for the desired blade depth. In this embodiment the height is adjusted by sliding the upper column 134 over the lower column 132; then rotating the upper column 134 about the lower column 132 so that the pin 136 slides into a j-shaped slot 138 at the desired blade depth setting. The height may also be adjusted by other means depending on the configuration. For example, where the upper 134 and lower 132 portions have mating threads, the height can be adjusted by screwing the upper portion 134 onto the lower portion 132. The last step 170 is sliding the retractor onto the blade extending tower to extend the telescoping or extendable blades. In certain embodiments the method further includes the step 150 of determining a desired blade depth.

Figure 7:
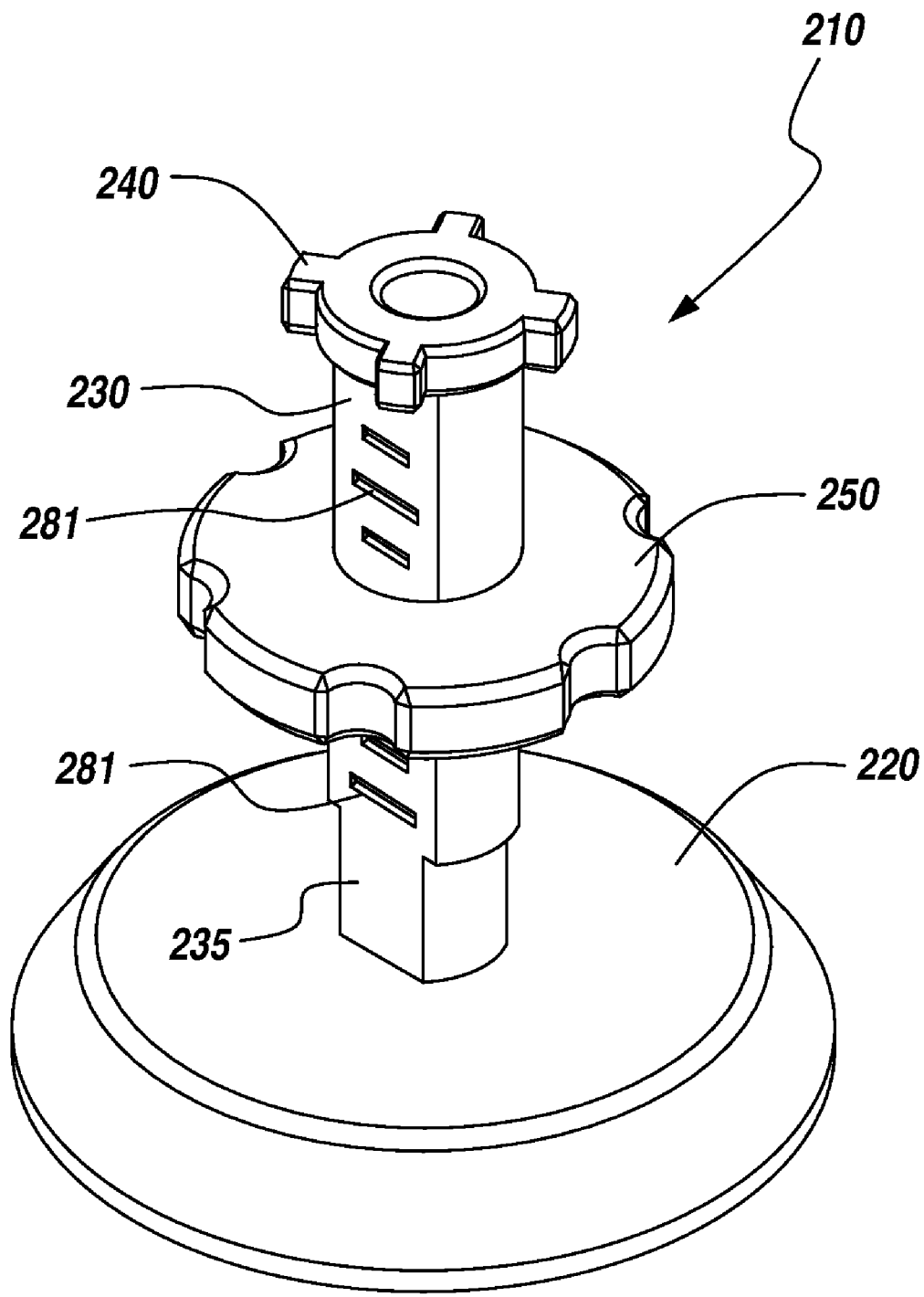
FIG. 7 is a perspective view of a blade extending tower having an adjustable stop according to an embodiment of the invention.

In certain embodiments, such as depicted in FIG. 7, the blade extending tower 210 features a base 220, a column 230 extending substantially perpendicular from the base 220, mating features 240 on the column 230 configured to engage the blades of a retractor, and an adjustable stop 250 configured to be positioned along the length of the column 230. The stop 250 is used set the depth of the retractor blades by stopping the progress of a retractor as it is slid or pushed onto the blade extending tower 210. In this embodiment the stop is a ring around the column 230 but the stop 250 may take any shape or configuration suitable to stop the progress of a retractor as it is slid or pushed onto the blade extending tower 210. Preferably the stop is formed of stainless steel or other surgical grade material like the rest of the blade extending tower 210.

The stop 250 can be secured in place along the column 230 to produce a desired blade depth using various configurations. In the embodiment of FIG. 7 the column 230 and stop 250 have mating threads allowing the stop to be screwed into location for a desired blade depth. The column 230 of this embodiment further has substantially flat sections 235 without threads. These sections 235 have graduations 231 to assist in the setting of blade depth. The column 230 also has a smooth section 232 for disengaging the mating threads of the adjustable stop 250 to aid in cleaning.

Figure 8:
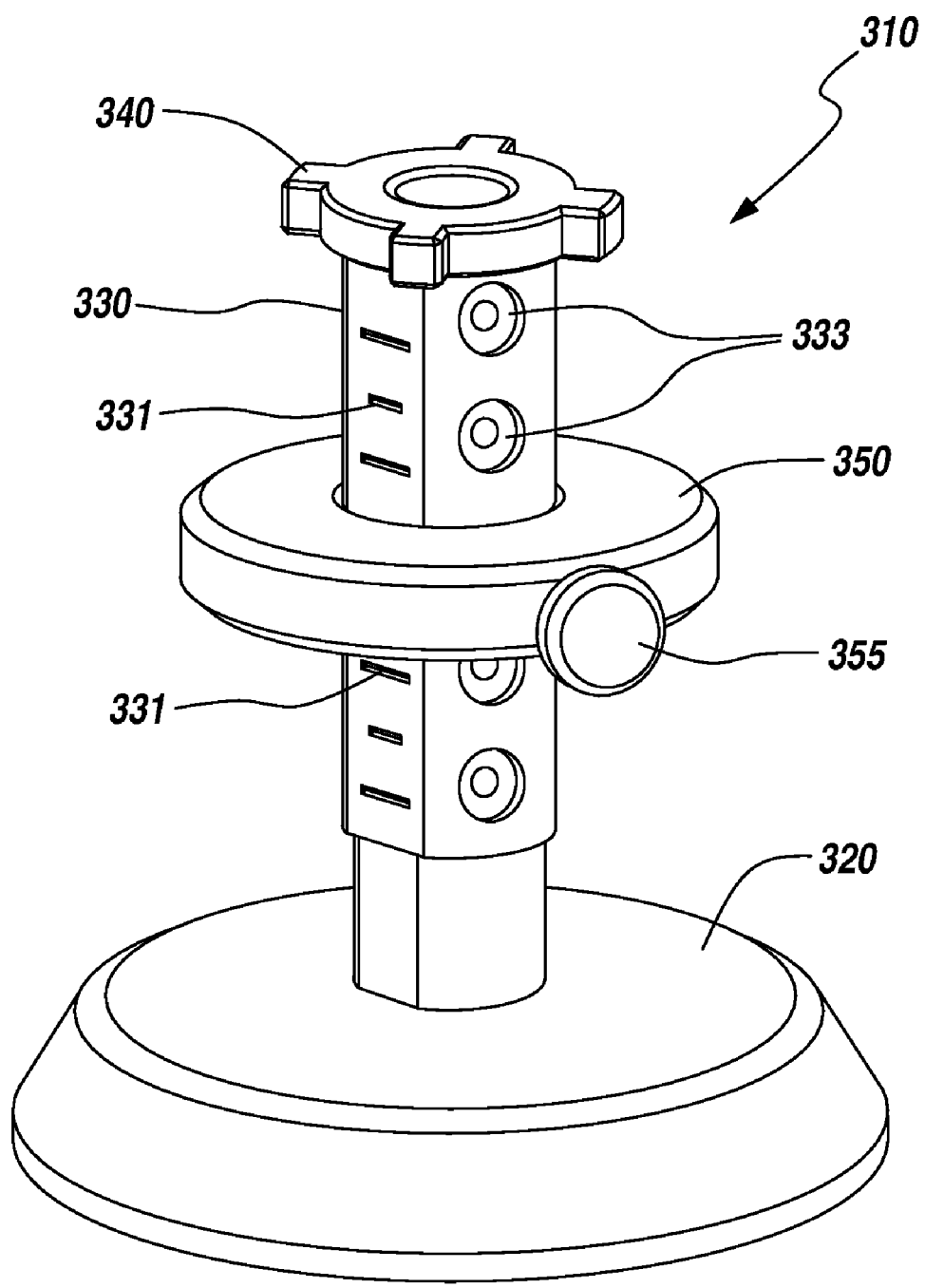
FIG. 8 is a perspective view of a blade extending tower having an adjustable stop according to another embodiment of the invention.

In another embodiment, as shown in FIG. 8, the blade extending tower 310 features a base 320, column 330, mating features 340, and an adjustable stop 350 which uses a spring loaded plunger 355 to fix the position of the stop 350. The adjustable stop 350 locks into features, here detents 333, in the column 330 at pre-defined graduations 331 using the spring-loaded plunger 355 that mates with the detents 333 in the column 330. Pulling the plunger radialy outward from the stop 350 releases the plunger from the detents 333 allowing the stop to be positioned along the length of the column 330. Releasing the plunger 355 allows the plunger 355 to mate with the detents 333 to again lock the stop 350 into position.

Figure 9:
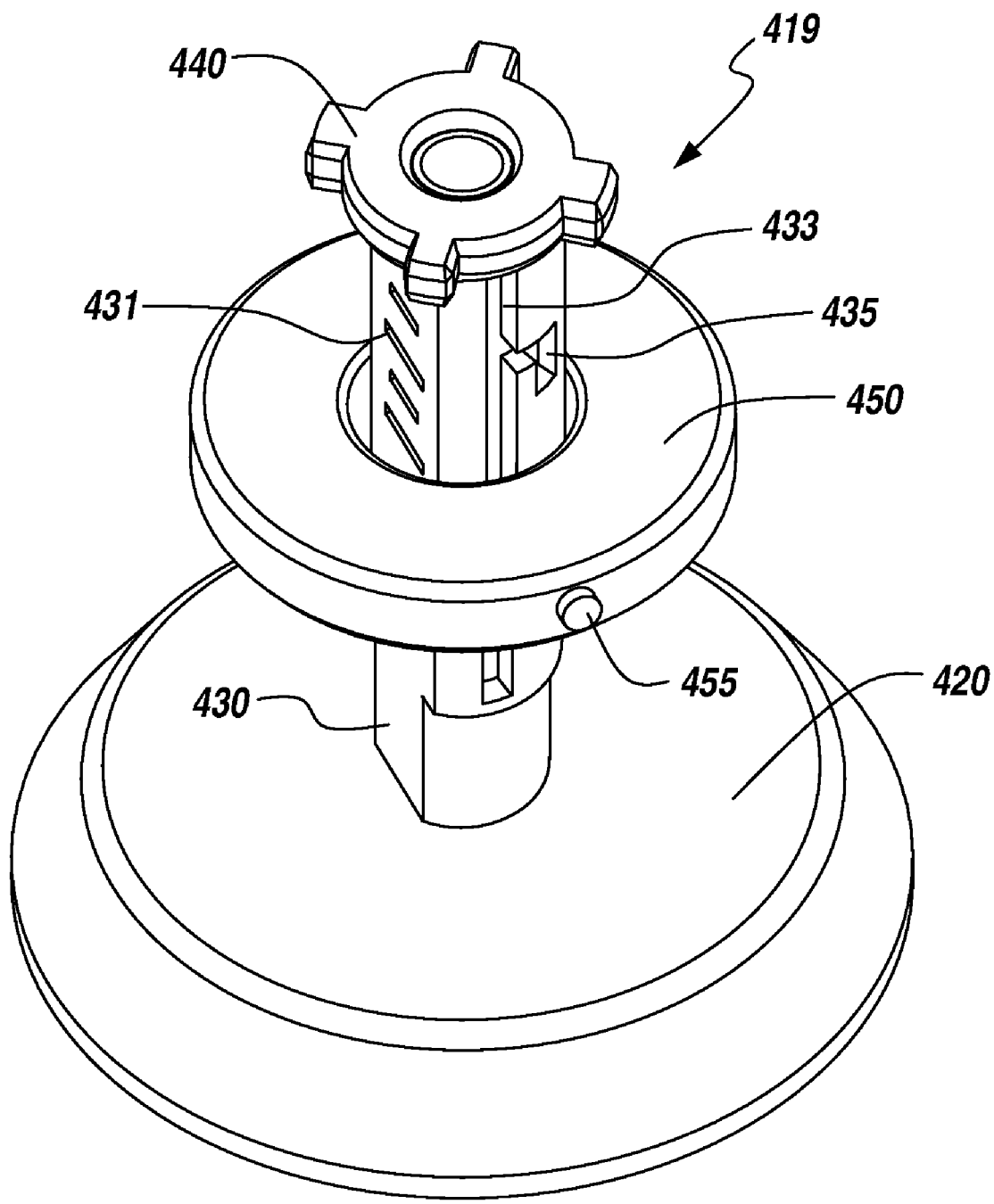
FIG. 9 is a perspective view of a blade extending tower having an adjustable stop according to another embodiment of the invention.

In another embodiment, as shown in FIG. 9, the blade extending tower 410 features a base 420, column 430, mating features 440, and an adjustable stop 450 which uses a pin 455 that slides in a groove 433 in the column 430. The stop 450 locks into pre-defined graduations 431 by rotating the stop 450 around the column 430 guiding the pin 455 into a j-shaped slot 435 on the column 430. Disengaging the pin 455 from the j-shaped slot 435 allows the stop 450 to once again move along the length of the column 430.

Figure 10:
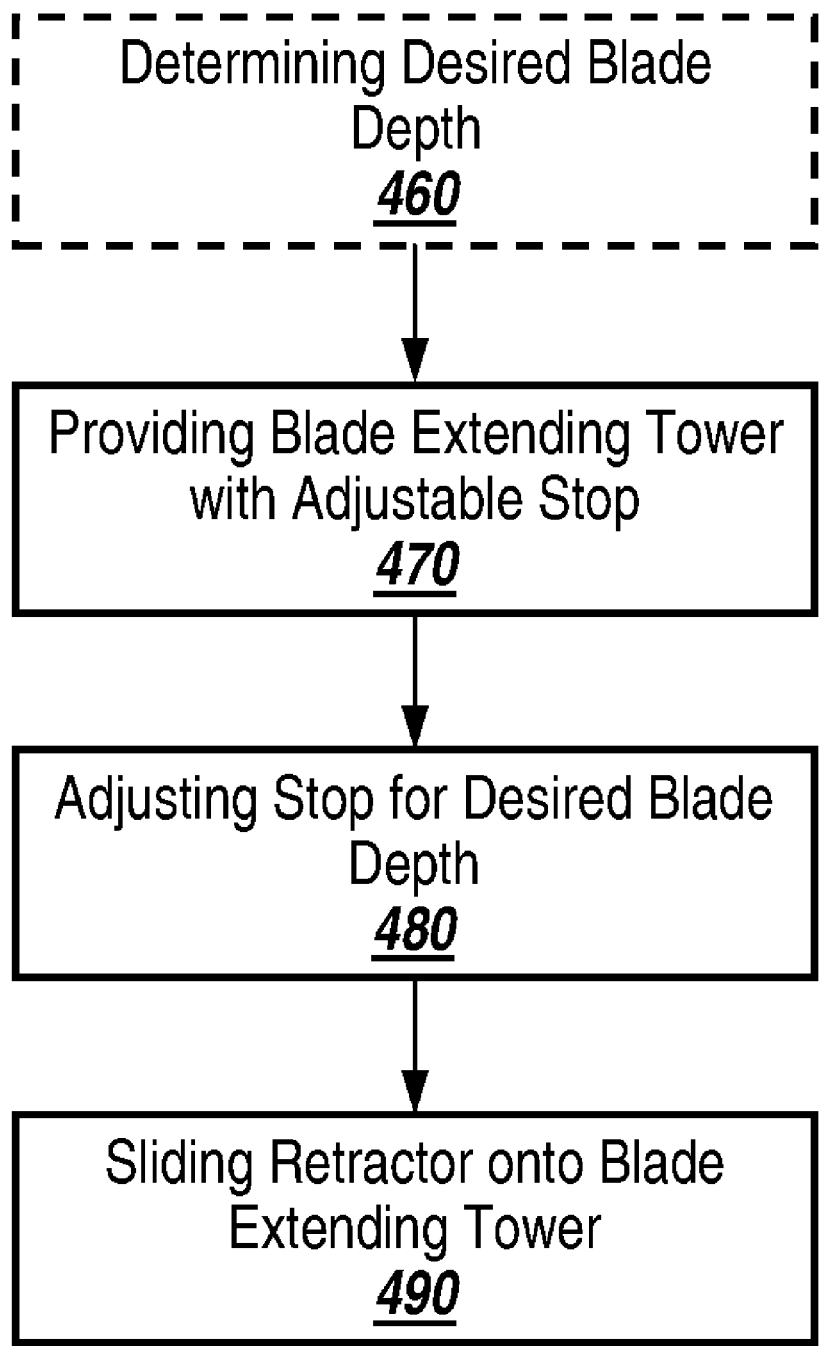
FIG. 10 is a flow chart depicting one embodiment of a method of setting blade depth on a retractor having telescoping or extendable blades using the blade extending tower of FIGS. 7-9.

FIG. 10 is a block diagram flow chart depicting one embodiment of a method of setting blade depth on a retractor having telescoping or extendable blades using a blade extending tower as depicted in FIG. 7. It should be noted that this method may be applied to the embodiments of the blade extending towers depicted in FIGS. 8 and 9 as well. The first step 470 is providing a blade extending tower 210 consisting of a base 220, a column extending substantially perpendicular from the base 230, mating features 240 on the column 230 configured to engage the blades of a retractor, and an adjustable stop 250 configured to be positioned along the length of the column 230. The next step 480 is adjusting the stop 250 to provide a desired depth for the retractor blades. For the embodiment of the blade extending tower of FIG. 7, this involves screwing the stop 250 to the proper location on the column 230 for the desired blade depth. For the embodiment depicted in FIG. 8 this involves using the spring plunger 355 to set the stop 350 at the proper location on the column 330 for the desired blade depth. For the embodiment depicted in FIG. 9 this involves guiding the pin 455 into a j-shaped slot 435 on the column 430 to set the stop 450 at the proper location on the column 430 for the desired blade depth. The final step 490 is sliding the retractor onto the blade extending tower all the way to the stop 250, 350, or 450 to extend the telescoping or extendable blades. In certain embodiments the method further includes the step 460 of determining a desired blade depth. This is typically accomplished by the surgeon who will measure the required blade depth from the patient's skin level to the anatomy being targeted.

Figure 11:
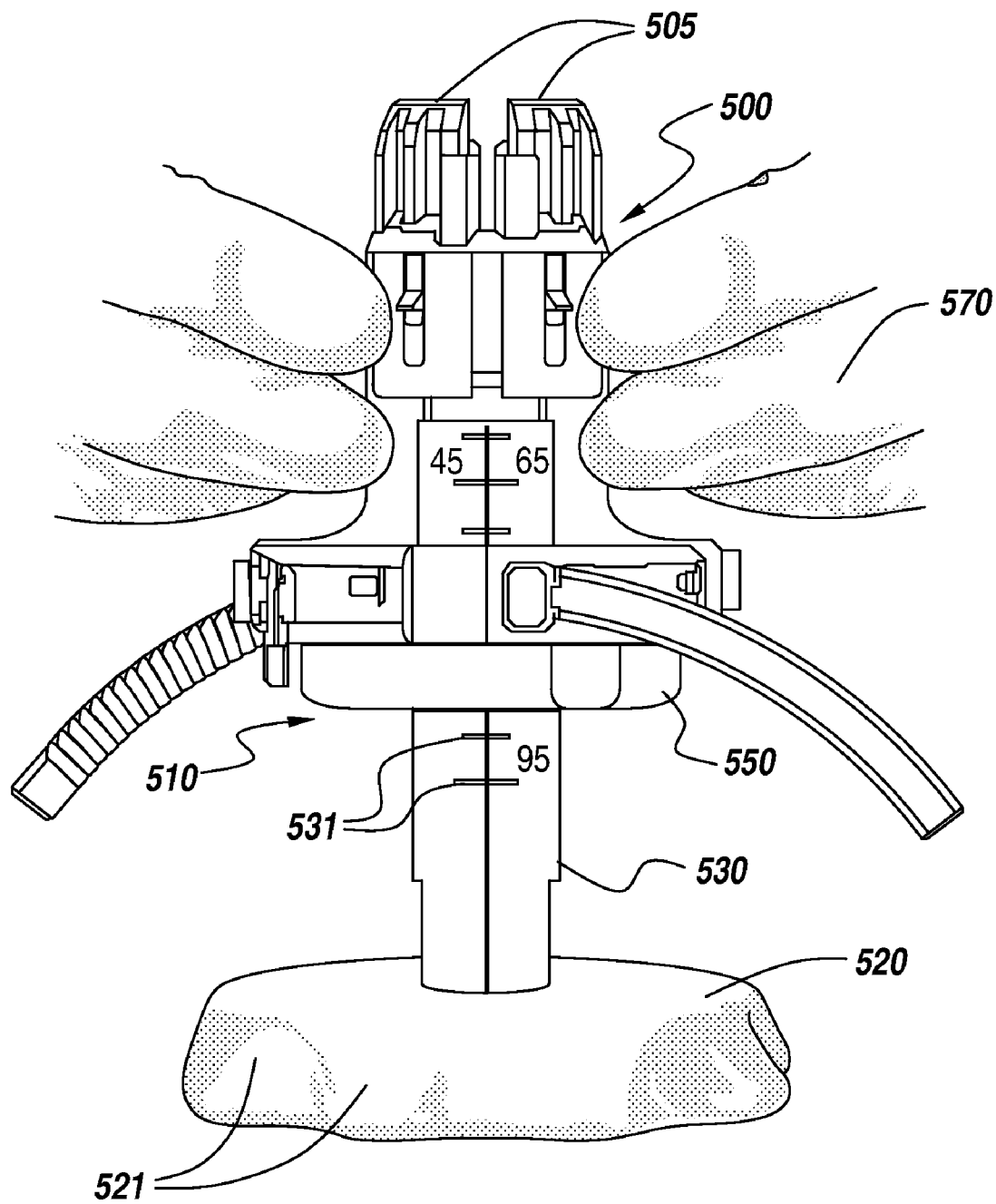
FIG. 11 is a visual depiction of a retractor being placed or slid onto a blade extending tower having an adjustable stop to set blade depth.

FIG. 11 is a visual depiction of a retractor being placed or slid onto the blade extending tower 510 as set forth in step 490 in FIG. 10. Here the retractor 500 has four telescoping blades 505. The blade extending tower 510 has an adjustable stop 550 set for a desired blade depth as indicated by the graduations 531 on the column 530. In this embodiment the base 520 has surface features 521. Here the blade extending tower 510 is placed on a stable surface and the retractor 500 is slid onto the blade extending tower 510 by a user, here a surgeon or technician 570. In operation when the retractor 500 is pushed or slid onto the column 530 of the blade extending tower 510, the mating features 540 (not shown) engage the blades 505 of the retractor 500 effectively stopping the movement of the blades 505 while the rest of the retractor 500 continues along the length of the column 530 until stopped by the adjustable stop 550. In this manner the blades 505 are extended to the depth determined by location of the stop 550.

Figure 12:
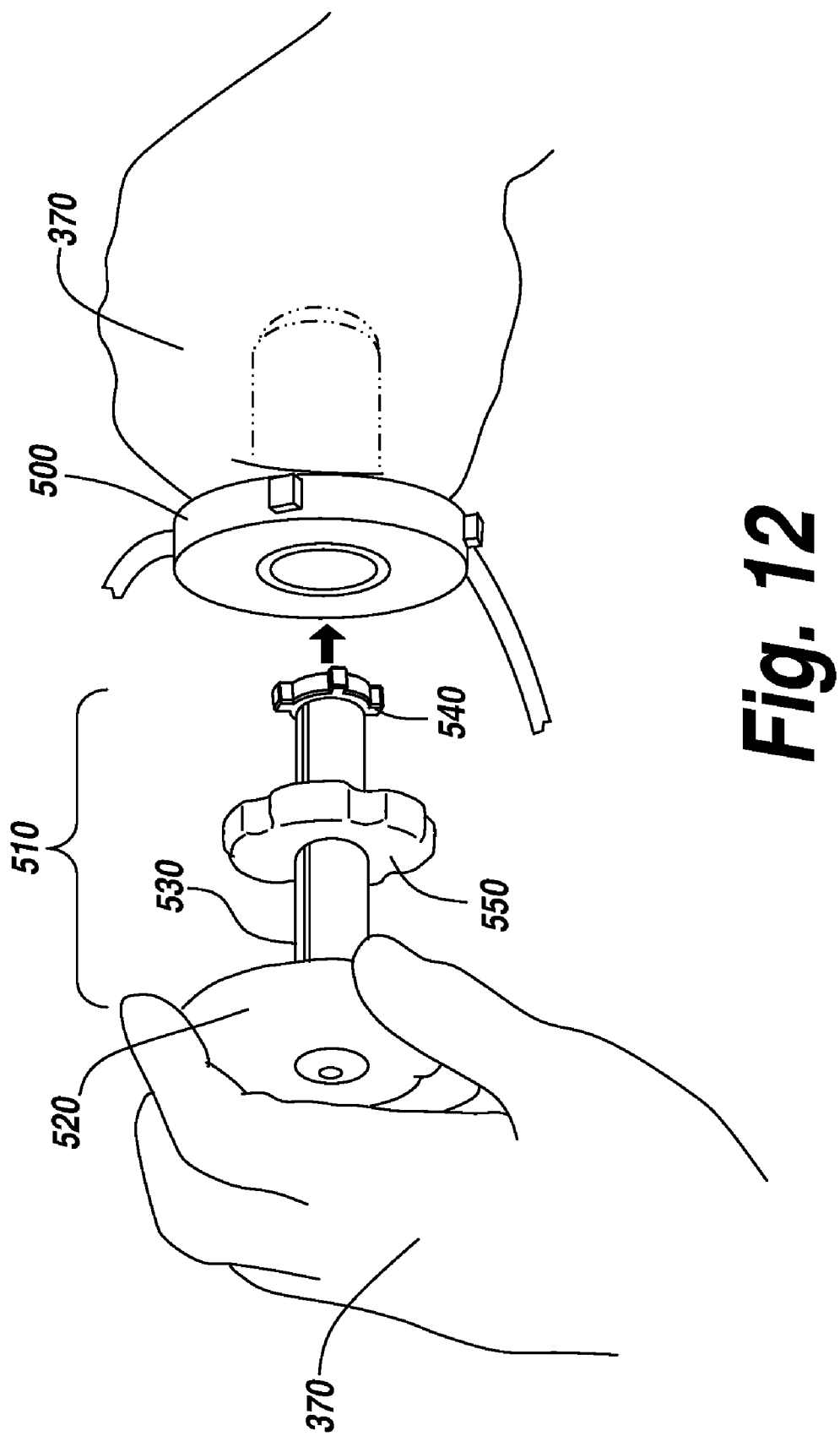
FIG. 12 is a visual depiction of another method of placing or sliding a retractor onto a blade extending tower having an adjustable stop to set blade depth.

FIG. 12 is visually depicting another method of placing or sliding retractor onto a blade extending tower 510 as set forth in step 490 in FIG. 10. Here the blade extending tower 510 is held by a user, here a surgeon or technician 570, in one hand and the retractor 500 is slid onto the blade extending tower 510 by the surgeon or technician 570 using the other hand. In operation when the retractor 500 is pushed or slid onto the column 530 of the blade extending tower 510, the mating features 540 engage the blades 505 (not shown) of the retractor 500 effectively stopping the movement of the blades 505 while the rest of the retractor 500 continues along the length of the column 530 until stopped by the adjustable stop 550. In this manner the blades 505 are extended to the depth determined by location of the stop 550.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense. For example, one skilled in the art will recognize that the instrument of the illustrative embodiment of the invention is not limited to use in percutaneous insertion and removal.

It is also to be understood that the following claims are to cover all generic and specific features of the invention described herein, and all statements of the scope of the invention which, as a matter of language, might be said to fall therebetween.

The invention claimed is:

1. A method of setting blade depth on a retractor having a plurality of extendable blades, the method comprising:
   determining an amount of extension for the plurality of extendable blades, and
   positioning the retractor on a blade extending tower to extend the plurality of extendable blades of the retractor an amount approximate to the determined amount of extension for the plurality of extendable blades, the blade extending tower including a base, a column extending from the base, and mating features on the column configured to engage the plurality of extendable blades of the retractor to extend the plurality of extendable blades to a desired blade length.

2. The method of claim 1, further comprising adjusting an adjustable stop of the instrument a distance from a base of the instrument approximate to the determined amount of extension for the plurality of extendable blades.

3. The method of claim 1, further comprising inserting the retractor into an incision made in a patient.

4. A method of setting blade depth on a retractor having extendable blades, the method comprising:
   providing a blade extending tower comprising a base, a column extending substantially perpendicular from the base, mating features on the column configured to engage the blades of a retractor to extend the blades to a desired blade length, and an adjustable stop configured to be positioned along the length of the column to stop the progress of a retractor placed onto the blade extending tower;
   adjusting the stop to provide a desired length for the retractor blades; and
   sliding the retractor onto the blade extending tower to the adjusted stop to extend the blades of the retractor.

* * * * *

UNITED STATES PATENT AND TRADEMARK OFFICE
CERTIFICATE OF CORRECTION

| | | |
|---|---|---|
| PATENT NO. | : 7,625,339 B2 | Page 1 of 1 |
| APPLICATION NO. | : 11/014615 | |
| DATED | : December 1, 2009 | |
| INVENTOR(S) | : Frasier et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 738 days.

Signed and Sealed this

Twenty-first Day of December, 2010

David J. Kappos
*Director of the United States Patent and Trademark Office*